United States Patent [19]

Felman et al.

[11] Patent Number: 5,389,671
[45] Date of Patent: Feb. 14, 1995

[54] 4- OR 5-(SUBSTITUTED SULFONYL)METHYL-3(2H)-FURANONES

[75] Inventors: Steven W. Felman, Langhorne, Pa.; Ivo L. Jirkovsky, Plainsboro; Kevin A. Memoli, Cranbury, both of N.J.

[73] Assignee: American Home Products Corporation, Madison, N.J.

[21] Appl. No.: 197,427

[22] Filed: Feb. 16, 1994

Related U.S. Application Data

[62] Division of Ser. No. 986,644, Dec. 8, 1992, Pat. No. 5,314,913.

[51] Int. Cl.$^6$ ............................................. A61K 31/34
[52] U.S. Cl. ...................................................... 514/473
[58] Field of Search ......................................... 514/473

[56] References Cited

U.S. PATENT DOCUMENTS 4,966,905 10/1990 Felman et al. .................... 514/314

Primary Examiner—C. Warren Ivy
Assistant Examiner—Ba K. Trinh
Attorney, Agent, or Firm—Richard K. Jackson

[57] ABSTRACT

The present invention relates to novel 4- or 5-(substituted sulfonyl) methyl-3(2H)-furanones having the formula (I)

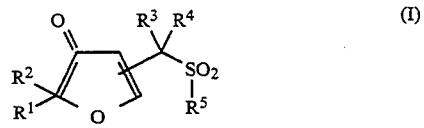

wherein $R^1$ and $R^2$ are independently alkyl containing 1 to 6 branched or straight chain carbon atoms, phenyl, or halogen substituted phenyl; or $R^1$ and $R^2$ are joined by 5 to 7 carbon atoms;

$R^3$ and $R^4$ are independently hydrogen, alkyl containing 1 to 6 branched or straight chain carbon atoms or $R^3$ and $R^4$ are joined by 4 to 6 carbon atoms;

$R^5$ is alkyl containing 1 to 6 branched or straight chain carbon atoms, phenyl, naphthyl or substituted phenyl wherein the substituent is selected from the group consisting of alkyl containing 1 to 6 branched or straight chain carbon atoms, halogen, methoxy, nitro and acetamide which possess blood-glucose lowering activity and inhibit cholesterol absorption, and which have cytoprotective and antiulcer activity, to processes for preparation thereof, pharmaceutical compositions comprising the same, and to the method of using the same in the reduction of excess glucose and cholesterol and of treatment of ulcers in human beings and animals.

1 Claim, No Drawings

4- OR 5-(SUBSTITUTED SULFONYL)METHYL-3(2H)-FURANONES

This is a division of application Ser. No. 07/986,644, filed Dec. 8, 1992, was U.S. Pat. No. 5,314,913.

SUMMARY OF INVENTION

The present invention relates to novel 4- or 5-(substituted sulfonyl) methyl-3(2H)-furanones which possess blood-glucose lowering activity and inhibit cholesterol absorption, and which have cytoprotective and antiulcer activity, to processes for preparation thereof, pharmaceutical compositions comprising the same, and to the method of using the same in the reduction of excess glucose and cholesterol and of treatment of ulcers in human beings and animals.

The compounds of the present invention have the formula (I)

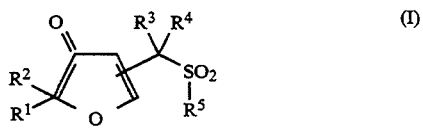

wherein $R^1$ and $R^2$ are independently alkyl containing 1 to 6 branched or straight chain carbon atoms, phenyl, or halogen substituted phenyl; or $R^1$ and $R^2$ are joined by 5 to 7 carbon atoms;

$R^3$ and $R^4$ are independently hydrogen, alkyl containing 1 to 6 branched or straight chain carbon atoms or $R^3$ and $R^4$ are joined by 4 to 6 carbon atoms;

$R^5$ is alkyl containing 1 to 6 branched or straight chain carbon atoms, phenyl, naphthyl or substituted phenyl wherein the substituent is selected from the group consisting of alkyl containing 1 to 6 branched or straight chain carbon atoms, halogen, methoxy, nitro and acetamide.

The compounds of the present invention of formula (I):
wherein $R^1$ and $R^2$ are independently alkyl containing 1 to 3 carbon atoms, phenyl or $R^1$ and $R^2$ are joined by 5 to 7 carbon atoms;
$R^3$ and $R^4$ are independently hydrogen, alkyl containing 1 to 3 carbon atoms or $R^3$ and $R^4$ are joined by 4 to 6 carbon atoms;
$R^5$ is phenyl, naphthyl or substituted phenyl wherein the substituent is selected from the group consisting of methoxy, nitro and acetamide possess blood-glucose lowering activity and inhibit cholesterol absorption.

The preferred compounds of the present invention for lowering blood-glucose levels and inhibiting cholesterol absorption are designated:
1. 2,2-Dimethyl-4-(phenylsulfonyl)methyl-3(2H)-furanone
2. 2,2-Dimethyl-4-[(1-naphthalenyl)sulfonyl]methyl-3(2H)-furanone
3. 2,2-Dimethyl-4-[(2-methoxyphenyl)sulfonyl]methyl-3(2H)-furanone
4. 2,2-Dimethyl-4-[(4-nitrophenyl)sulfonyl]methyl-3(2H)-furanone
5. N-[[(4,5-Dihydro-5,5-dimethyl-4-oxo-3-furanyl)methyl]sulfonyl]phenyl acetamide
6. 3-(Phenylsulfonyl)methyl-1-oxaspiro[4,5]decan-4-one
7. 2,2-Dimethyl-5-(phenylsulfonyl)methyl-3(2H)-furanone
8. 2,2-Dimethyl-5-[1-methyl-1-(phenylsulfonyl)ethyl]-3(2H)-furanone
9. 2,2-Dimethyl-5-[1-(phenylsulfonyl)-1-cyclopentyl]methyl-3(2H)-furanone and
10. 2-Methyl-2-phenyl-5-(phenylsulfonyl)methyl-3(2H)-furanone.

The compounds of the present invention of formula (I): wherein $R^1$ and $R^2$ are independently alkyl containing 1 to 3 carbon atoms, phenyl or halogen substituted phenyl;
$R^3$ and $R^4$ are hydrogen;
$R^5$ is alkyl containing 1 to 6 branched or straight chain carbon atoms, substituted phenyl wherein the substituent is selected from the group consisting of alkyl containing 1 to 6 branched or straight chain carbon atoms and halogen possess cytoprotective and antiulcer activity.

The preferred compounds of the present invention that possess cytoprotective and antiulcer activity are designated:
11. 5-[(4-Chlorophenyl)sulfonyl]methyl-2,2-dimethyl-3(2H)-furanone
12. 5-[(4-Fluorophenyl)sulfonyl]methyl-2,2-dimethyl-3(2H)-furanone
13. 2,2-Dimethyl-5-(methylsulfonyl)methyl-3(2H)-furanone
14. 2,2-Dimethyl-5-[[4-(1,1-dimethylethyl)phenyl]sulfonyl]methyl-3(2H)-furanone
15. 4-[(4-Fluorophenyl)sulfonyl]methyl-2,2-dimethyl-3(2H)-furanone
16. 2,2-Dimethyl-4-[[4-(1,1-dimethylethyl)phenyl]sulfonyl]methyl-3(2H)-furanone
17. 4-[(1,1-Dimethylethyl)sulfonyl]methyl-2,2-dimethyl-3(2H)-furanone
18. 4-[(1,1-Dimethylethyl)sulfonyl]methyl-2-(4-fluorophenyl)-2-methyl-3(2H)-furanone
19. 4-[(1,1-Dimethylethyl)sulfonyl]methyl-2-(4-chlorophenyl)-2-methyl-3(2H)-furanone
20. 4-[(1,1-Dimethylethyl)sulfonyl]methyl-2-methyl-2-phenyl-3(2H)-furanone.

The present invention also provides pharmaceutical compositions which comprises a compound of this invention and a pharmaceutically acceptable carrier. In particular, the present invention provides pharmaceutical compositions which possess blood-glucose lowering activity and inhibit cholesterol absorption, and which have cytoprotective and antiulcer activity which comprises an effective amount of a compound of this invention and a pharmaceutically acceptable carder.

The compositions are preferably adapted for oral administration. However, they may be adapted for other modes of administration, for example parenteral administration.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 1 to 50 mg. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compounds may also be administered in a parenteral dosing form.

The compositions of the invention may be formulated with conventional excipients, such as a filler, a disintegrating agent, a binder, a lubricant, a flavoring agent and the like.

The present invention further provides a compound of the invention for use as an active therapeutic substance. Compounds described in this invention are of particular use in the lowering of blood-glucose and inhibiting cholesterol absorption. They can also be used for their cytoprotective and antiulcer activity.

The present invention further provides a method of lowering blood-glucose and inhibiting cholesterol absorption in mammals including man, which comprises administering to the afflicted mammal an effective amount of a compound or a pharmaceutical composition of the invention.

The present invention further provides a method of treating ulcers in mammals including man, which comprises administering to the afflicted mammal an effective amount of a compound or a pharmaceutical composition of the invention.

The compounds of the present invention are prepared by the following Synthetic Schemes:

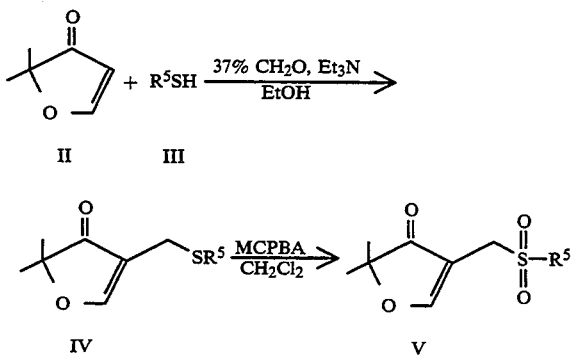

wherein $R^5$ is as defined above

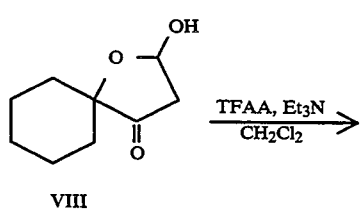

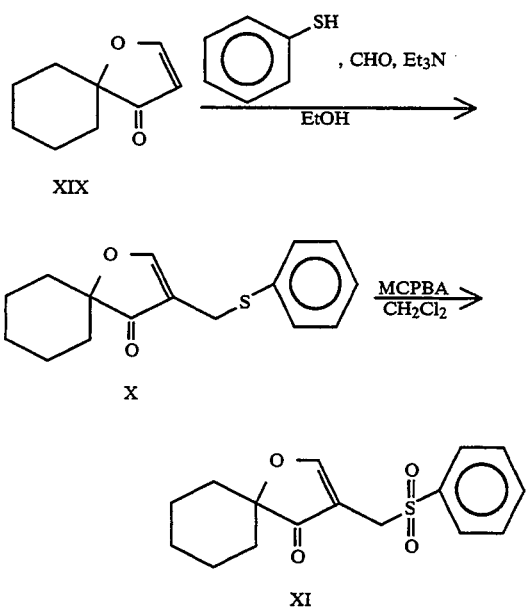

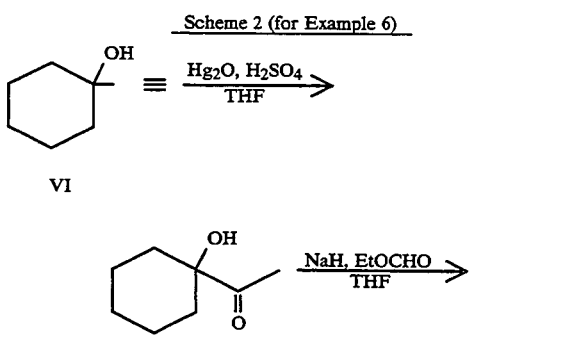

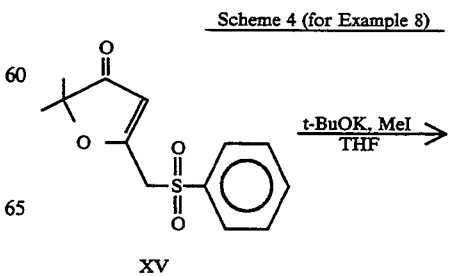

-continued
Scheme 4 (for Example 8)
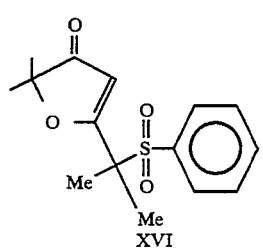
XVI
Scheme 5 (for Example 9)
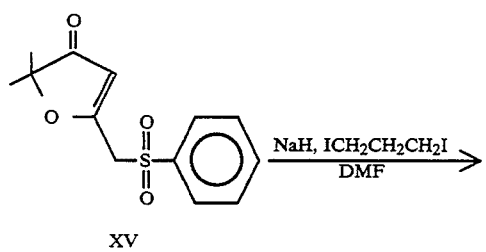
XV
XVII
Scheme 6 (for Example 10)
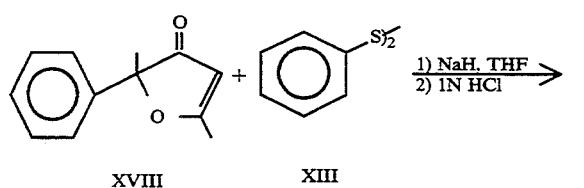
XVIII    XIII
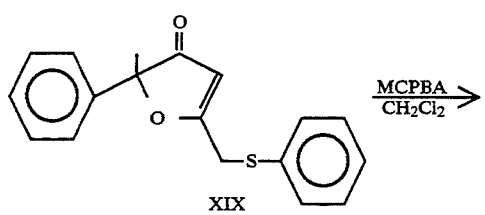
XIX
XX
Scheme 7 (for Examples 11 to 12)
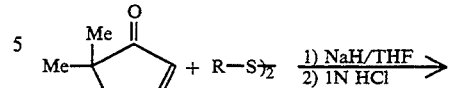
IIA    IIIA
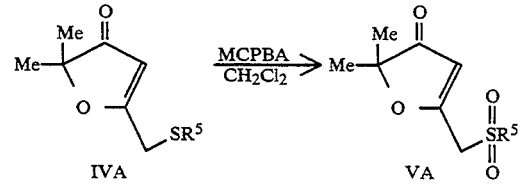
IVA    VA
$R^5$ is as defined above
Scheme 8 (for Examples 13 to 14)
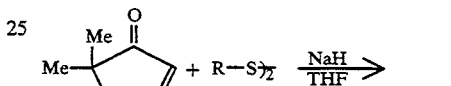
IIA    IIIA
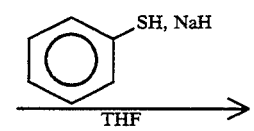
VIA
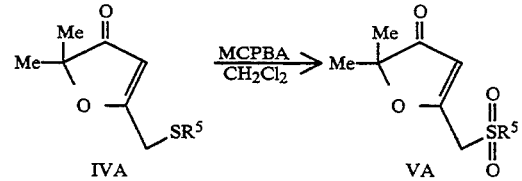
IVA    VA
$R^5$ is as defined above
Scheme 9 (for Examples 15 to 17 and 19 to 20)
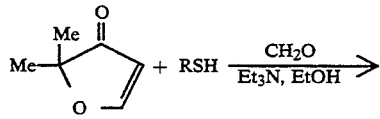
VIIA    VIIIA
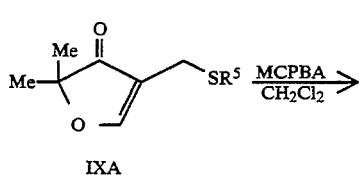
IXA

-continued
Scheme 9 (for Examples 15 to 17 and 19 to 20)

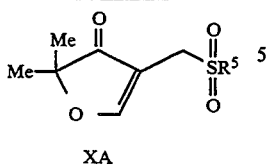

XA

R[5] is as defined above

Scheme 10 (for Example 18)

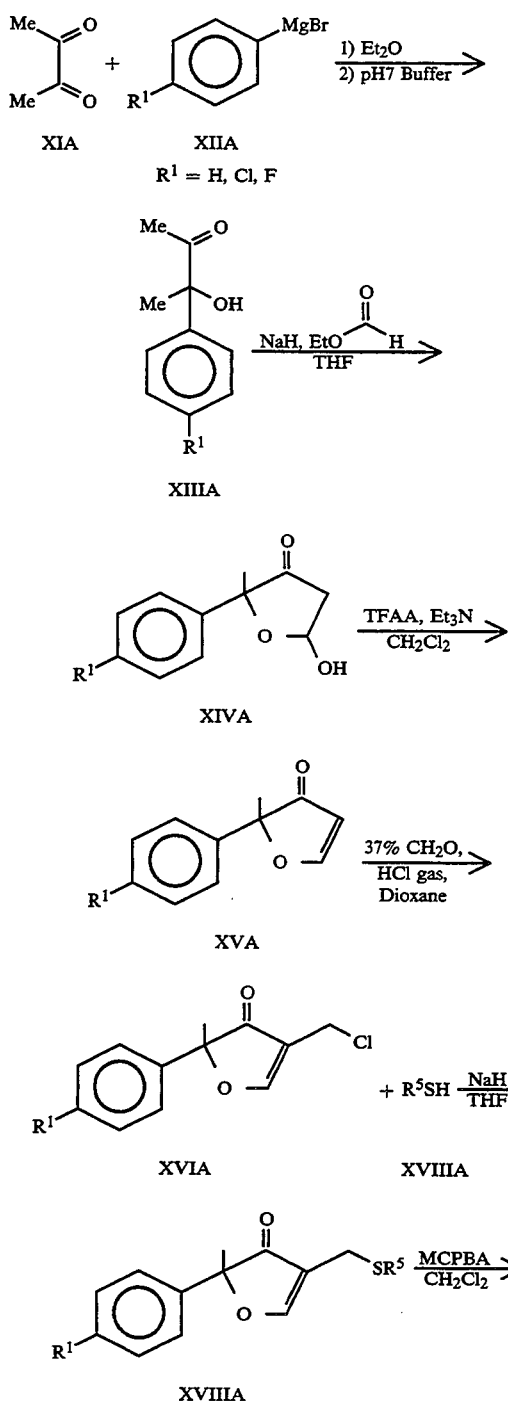

-continued
Scheme 10 (for Example 18)

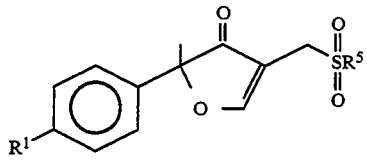

XIXA

R[5] is as defined above

The following Examples further illustrate this invention.

EXAMPLE 1

2,2-Dimethyl-4-(phenylsulfonyl)methyl-3(2H)-furanone

A solution of 2,2-dimethyl-3(2H)-furanone (5.0 g, 44.6 mmol), thiophenol (4.9 g, 44.6 mmol), aqueous formaldehyde (37%, 7.2 g, 89.2 mmol) and triethylamine (4.5 g, 44.6 mmol) in 95% ethanol (100 mL) was heated at reflux for one day. More aqueous formaldehyde (37%, 7.2 g, 89.2 mmol) was added and the solution was heated at reflux for another day. After the reaction was cooled to room temperature, the solution was concentrated to 50 mL then diluted with saturated aqueous sodium chloride (100 mL). The solution was extracted with ether (3×100 mL). The combined ethereal extracts were washed with 1N aqueous hydrochloric acid (2×25 mL) and saturated aqueous sodium chloride (75 mL). The resulting ethereal solution was dried over magnesium sulfate, filtered and concentrated under reduced pressure to yield an orange liquid. The crude product was purified by column chromatography (silica gel, pet. ether then ether) to yield a yellow orange liquid (9.0, 86%). $^1$H NMR (CDCl$_3$, 200 MHz): δ1.30 (s, 6H), 3.63 (d, J=2 Hz, 2H), 7.25 (m, 5H), 7.85 (br s, 1H).

To a solution of sulfide (9.0 g, 38 mmol) in dichloromethane (250 mL) was added m-chloroperbenzoic acid (85%, 16.6 g, 96 mmol). After the reaction was stirred two hours, the reaction was filtered. The resulting solution was washed with 0.5N aqueous sodium sulfite (50 mL) and saturated aqueous sodium bicarbonate (2×50 mL). The solution was dried over magnesium sulfate, filtered and concentrated under reduced pressure to give a yellow solid. The crude product was purified by column chromatography (silica gel, pet. ether/ethyl acetate) to afford a yellow solid (2.4 g 23%). An analytically pure sample was obtained by trituration with ether m.p. 139°–141° C. $^1$H NMR (CDCl$_3$, 400 MHz): δ1.22 (s, 6H), 3.96 (s, 2H), 7.52 (t, J=8 Hz, 2H), 7.63 (t, J=8 Hz, 1H), 7.83 (d, J=7.2 Hz, 2H), 8.37 (s, H); Analysis calc'd for C$_{13}$H$_{14}$O$_4$S: C, 58.63; H, 5.30%; Found: C, 58.28; H, 5.37%.

The compounds of Examples 2 through 5 were prepared by the procedure described in Example 1 using the appropriate thiol (III).

EXAMPLE 2

2,2-Dimethyl-4-[(1-naphthalenyl)sulfonyl]methyl-3(2H)-furanone

Prepared in 16% yield; m.p. 138°–140° C.; MS (EI): 316 (M+), 125 (100). $^1$H NMR (CDCl$_3$, 400 MHz): δ1.15 (s, 3H), 1.65 (s, 3H), 4.15 (s, 2H), 7.55 (dd, J$^1$=10 Hz, J$^2$=10 Hz, 7H), 7.64 (t, J$_1$=6 Hz, 1H), 7.95 (d, J=6

Hz, 1H), 8.12 (J=6 Hz, 1H), 8.17 (J=6 Hz, 1H), 8.31 (s, 1H), 8.8 (d, J=6 Hz, 1H); Analysis calc'd for $C_{17}H_{16}O_4S$: C, 64.54%; H, 5.10; Found: C, 64.67; H, 4.76%.

EXAMPLE 3

4-[(2-Methoxyphenyl)sulfonyl]methyl-2,2-dimethyl-3(2H)-furanone

Prepared in 24% yield; m.p. 112°–113° C.; MS (EI): 296 (M+), 125 (100). $^1$H NMR (CDCl$_3$, 400 MHz): δ1.25 (s, 6H), 4.10 (s, 3H), 4.22 (s, 2H), 7.02 (m, 2H), 7.55 (t, J=8 Hz, 1H), 7.78 (d, J=8 Hz, 1H), 8.31 (s, 1H).

EXAMPLE 4

2,2-Dimethyl-4-[(4-nitrophenyl)sulfonyl]methyl-3(2H)-furanone

Prepared in 18% yield; m.p. 184°–185° C.; MS (EI): 311 (M+), 125 (100). $^1$H NMR (CDCl$_3$, 400 MHz): δ1.23 (s, 6H), 4.05 (s, 2H), 8.04 (d, J=4 Hz, 2H), 8.36 (d, J=4 Hz, 2H), 8.42 (s, 1H); Analysis calc'd for $C_{13}H_{13}O_6NS$: C, 50.16; H, 4.21; N, 4.50%; Found: C, 50.38; H, 4.14; N, 4.51%.

EXAMPLE 5

N-[[(4,5-Dihydro-5,5-dimethyl-4-oxo-3-furanyl)methyl]sulfonyl]phenyl-acetamide

Prepared in 15% yield; m.p. 184°–185° C.; MS (EI): 323 (M+), 125 (100). $^1$H NMR (CDCl$_3$, 400 MHz): δ1.25 (s, 6H), 2.20 (s, 3H), 3.85 (S, 2H), 7.45 (br s, 1H), 7.74 (d, J=4 Hz, 2H), 7.75 (d, J-4 Hz; 2H), 7.75 (d, J=4 Hz, 2H), 8.38 (s, 1H).

EXAMPLE 6

3-(Phenylsulfonyl)methyl-1-oxospiro[4,5]decan-4-one

Mercuric oxide (5.0 g, 23 mM) was suspended in a solution of tetrahydrofuran (350 mL) and water (25 mL). After concentrated sulfuric acid (7.5 g) was added, the mixture was heated at reflux for 15 minutes. The mixture temperature was adjusted to 55° C., then a solution of 1-ethynyl-1-cyclohexanol (50 g, 0.40M) in tetrahydrofuran (250 mL) was added at a rate to maintain the reaction mixture temperature between 55°–60° C. After the addition, the reaction mixture was heated at 60° C. for 2 hours. The reaction was cooled to room temperature and filtered through celite. The filtrate was diluted with ether (500 mL) and the solution was extracted with saturated aqueous sodium chloride (3×100 mL). The resulting organic layer was dried over magnesium sulfate, filtered and concentrated under reduced pressure to give a yellow liquid. The crude product was distilled (73°–74° C., 3 mm) to give a clear liquid (43.6 g, 77%). $^1$H NMR (CDCl$_3$, 200 MHz): δ1.70 (m, 10H), 2.25 (s, 3H), 3.57 (s, 1H).

To a mixture of sodium hydride (50%, 5.8 g 120 mM) in tetrahydrofuran (200 mL) at 40° C., was added a solution of ketoalcohol (10 g, 70.4 mM) and ethyl formate in (5.2 g, 70.4 mM) tetrahydrofuran (100 mL) maintaining the reaction temperature between 40°–45° C. After the addition, the reaction was heated at 40° C. for 2 hours. The reaction was quenched with the addition of a solution of acetic acid (8.4 g) in water (100 mL) then cooled to room temperature. The solution was diluted with more water (300 mL) and ether (100 mL). After the layers were separated, the aqueous phase was extracted with ether (2×100 mL). The combined ethereal extract was washed with saturated aqueous sodium bicarbonate (50 mL), saturated aqueous sodium chloride (50 mL) and dried over magnesium sulfate. The resulting mixture was filtered and concentrated under reduced pressure to give an amber oil (11.8 g, 99%). $^1$H NMR (CDCl$_3$, 200 MHz): δ1.22 (m, 10H), 2.67 (m, 2H), 4.75 (br s, 1H), 5.78 (d, J=2 Hz, 1H).

To a solution of lactol (11.8 g, 69.3) in dichloromethane (500 mL) was added trifluoroacetic anhydride (9.8 mL, 69.3 g) dropwise. After the reaction was stirred one hour, triethylamine (21.2 mL, 152 5 mM) was added dropwise. Again, the reaction stirred one hour. Then the solution was extracted with water (2×200 mL) and saturated aqueous sodium bicarbonate (50 mL). The resulting solution was dried over magnesium sulfate, filtered and concentrated under reduced pressure to give a dark red liquid. The crude enone was purified by column chromatography (silica gel, pet. ether-ethyl acetate) to yield a red liquid (5.2 g, 49% from ketoalcohol). $^1$H NMR (CDCl$_3$, 200 MHz): δ1.59 (m, 10H), 5.62 (d, J=2 Hz, 1H), 8.18 (d, J=2 Hz, 1H).

The resulting enone was subjected to the same reaction conditions to make the compound in Example 1 with the appropriate thiol (III).

Prepared in 43% yield; m.p. 134°–135° C.; MS (El): 306(M+), 165 (100). $^1$H NMR (CDCl$_3$, 400 MHz): δ1.49 (m, 10H), 3.97 (s, 2H), 7.52 (t, J=8 Hz, 2H), 7.63 (t, J=7.2 Hz, 1H), 7.84 (d, J=6 Hz, 2H), 8.40 (s, 1H); Analysis calc'd for $C_{16}H_{18}O_4S$: C, 62.72; H, 5.92%; Found: C, 62.92; H, 6.10%.

EXAMPLE 7

2,2-Dimethyl-5-(phenylsulfonyl)methyl-3(2H)-furanone

To a solution of diisopropylamine (8.4 mL, 59.6 mM) in tetrahydrofuran (150 mL) at −78° C., was added dropwise a 2.3M solution of n-butyllithium in hexane. After the addition, the solution was stirred ten minutes when hexamethylphosphoramide (10.5 mL, 59.6 mM) dropwise. Again, the solution was stirred ten minutes. Then 2,2,5-trimethyl-3(2H)-furanone (5.0 mL, 39.7 mM) was added. Again the solution was stirred thirty minutes when diphenyl disulfide (8.7 g, 39.7 mM) was added in small portions. After the reaction was allowed to warm to room temperature, the reaction solution was diluted with diethyl ether (150 mL). The resulting solution was extracted with water (2×50 mL), 1N aqueous hydrochloric acid (2×50 mL) and saturated aqueous sodium chloride (2×50 mL). The organic layer was then dried over MgSO$_4$, filtered and concentrated under reduced pressure to give a yellow liquid. The crude sulfide was purified by column chromatography (silica gel, hexane) to give an amber liquid (5.0 g, 55% yield. $^1$H NMR (CDCl$_3$, 100 MHz): δ1.48 (s, 6H), 3.95 (s, 2H), 5.51 (s, 1H), 7.64 (m, 5H).

To a solution of the above sulfide (8.2 g, 35 mM) in dichloromethane (200 mL) at −78° C., was added dropwise a solution of m-chloroperbenzoic acid (85%, 15.1 g, 87.5) in dichloromethane (100 mL). After the addition the reaction was warmed to 0° C. and stirred for thirty minutes. The reaction mixture was then filtered and extracted with 0.5N aqueous sodium sulfite solution (100 mL), saturated aqueous sodium bicarbonate (2×100 mL), saturated aqueous sodium chloride (50 mL), and 1N aqueous sodium hydroxide (2×100 mL). The combined sodium hydroxide extracts were washed with dichloromethane (2×50 mL) then acidified with 6N aqueous hydrochloric acid. The resulting acid solution was extracted with diethyl ether (3×100 mL). The combined ethereal extracts were washed with saturated aqueous sodium chloride (50 mL), dried over magnesium sulfate filtered and concentrated under reduced pressure to give a yellow solid. The crude furanyl phenyl sulfone was dissolved in diethyl ether (100 mL), then washed with saturated aqueous sodium bicarbonate (3×50 mL), dried over magnesium sulfate and concentrated under reduced pressure to afford a whim solid. The crude sulfone was purified by column chromatography (silica gel, pet. ether/ethyl acetate) to give a white solid (3.3 g, 35%); m.p. 88°–89° C. $^1$H NMR (CDCl$_3$, 400 MHz): δ1.20 (s, 6H), 4.27 (s, 2H), 5.56 (s, 1H), 5.76 (t, J=8 Hz, 2H), 7.70 (t, J=8 Hz, 1H), 7.89 (d, J=4 Hz, 2H); MS (EI): 266 (M+), 69 (100; IR (KBr): 3120, 2995, 2940, 11695, 1595, 1325, 1150, 740 cm$^{-1}$; Analysis calc'd for C$_{13}$H$_{14}$O$_4$S: C, 58.63; H, 5.30%; Found: C, 58.68; 5.25%.

EXAMPLE 8

2,2-Dimethyl-5-[1-methyl-1-(phenysulfonyl)ethyl]-3(2H)-furanone

To a solution of potassium t-butoxide (2.55 g, 22.5 mM) in tetrahydrofuran (100 mL) was added a solution 2,2-dimethyl-5-[(phenylsulfonyl)methyl]-3(2H)-furanone (4.0 g, 15 mM) in tetrahydrofuran. After the addition the reaction was stirred fifteen minutes then methyl iodide (9.3 mL, 0.15M) was added and the solution was stirred three hours. The reaction was diluted with H$_2$O (200 mL) and extracted with diethyl ether (3×100 mL). The combined ethereal extracts were washed with saturated aqueous sodium chloride (50 mL) and dried over MgSO$_4$. The resulting mixture was filtered and concentrated under reduced pressure to give a yellow waxy solid. The crude product was purified by column chromatography (silica gel, hexane/ethyl acetate) to afford a pale yellow solid (4.1 g, 91%). Trituration of the solid with a 10% solution of ethyl ether in pet. ether gave an analytically pure product; m.p. 92°–93° C. $^1$H NMR (CDCl$_3$, 400 MHz): δ1.28 (s, 6H), 1.69 (s, 6H), 5.57 (s, 1H), 7.55 (t, J=8.2 Hz, 2H), 7.69 (t, J=8.0 Hz, 1H), 7.84 (d, J=4 Hz, 2H); IR (KBr): 2995, 1705 1580, 1545, 1300, 1070, 605; MS (EI): 284 (M+), 153 (100); Analysis calc'd for C$_{15}$H$_{18}$O$_4$S: C, 61.20; H, 6.16%; Found: C, 61.16; H, 6.34%.

EXAMPLE 9

2,2-Dimethyl-5-[1-(phenylsulfonyl)-1-cyclopentyl]-3(2H)-furanone

To a solution of 2,2-dimethyl-5-(phenylsulfonyl)-methyl-3(2H)-furanone (4.4 g, 16.5 mM) in dimethylformamide (120 mL) was added sodium hydride (50%, 870 mg, 18.15 mM). The resulting solution was stirred for one hour when 1,4-diiodobutane (5.1 g, 16.5 mM) was added. The reaction was then stirred for 1.5 hours. Again sodium hydride (50%, 870 mg, 18.14 mM) was added and the reaction was stirred till no starting material was observed on thin-layer chromatography. The reaction was diluted with saturated aqueous sodium chloride (250 mL) and was extracted with diethyl ether (4×50 mL). The combined ethereal extract was washed with saturated aqueous sodium chloride (50 mL), was dried over magnesium sulfate and was filtered. The resulting filtrate was concentrated under vacuum to afford a brown crystalline product (5.2 g). This reaction was repeated on more 2,2-dimethyl-5-(phenylsulfonyl)-1-cyclopentyl]-3(2H)-furanone (1.0 g, 3.8 mM) to give a brown crystalline product (1.2 g). The combined crude products were purified by column chromatography (silica gel, pet. ether/ethyl acetate) to yield a light yellow crystalline product (2.5 g, 38%). An analytically pure sample was obtained by titration of the solid with a 10% solution of diethyl ether in pet. ether; m.p. 144°–145° C. $^1$H NMR (CDCl$_3$, 400 MHz): δ1.20 (s, 6H), 1.64 (m, 2H), 1.92 (m, 2H), 2.24 (m, 2H), 2.57 (m, 2H), 5.57 (s, 1H), 7.51 (t, J=8 Hz, 2H), 7.64 (t, J=8 Hz, 1H), 7.79 (d, J=4 Hz, 2H); IR (KBr): 3120, 2980, 2940, 1695, 1580, 1300, 1235, 720, 690; MS (EI): 320 (M+), 77 (100); Analysis calc'd for C$_{17}$H$_{20}$O$_4$S: C, 63.73; H, 6.29%. Found: C, 63.82; H, 6.27%.

EXAMPLE 10

2-Methyl-2-phenyl-5-(phenylsulfonyl)methyl-3(2H)-furanone

To a suspension of sodium hydride (60%, 6.7 g, 167 mM) in dry tetrahydrofuran (350 mL) at room temperature was added 2,5-dimethyl-2-phenyl-3(2H)-furanone (9.0 g, 47.8 mM, prepared as described in U.S. Pat. No. 4,906,905) and diphenyl disulfide (23 g, 105 mM). The resulting solution was stirred at room temperature for two hours. Then, 1N aqueous hydrochloric acid (100 mL) was added and the reaction was stirred thirty minutes. Another portion (50 mL) of 1N aqueous hydrochloride acid was added and the layers were separated. The aqueous acidic layer was extracted with diethyl ether (2×150 mL). The combined organic extracts were dried over magnesium sulfate, filtered and concentrated under reduced pressure to yield a dark amber oil. The crude product was purified by column chromatography (silica gel, pet. ether then diethyl ether) to afford a light amber oil (10.2 g, 72%). $^1$H NMR (CDCl$_3$, 100 MHz): δ1.62 (s, 3H), 3.85 (s, 0, 5.35 (s, 1H), 7.35 (m, 10H).

To a solution of the above furanyl phenyl sulfide (10.2 g, 34.4 mmol) in dichloromethane (500 mL) was added m-chloroperbenzoic acid (14.8 g, 86 mmol). The resulting reaction was stirred for two hours. The solution was washed with 0.5M aqueous sodium sulfite (50 mL) and saturated aqueous sodium bicarbonate (2×50 mL). The dichloromethane layer was dried over magnesium sulfate, filtered and concentrated under reduced pressure to yield a crude brown gum. The product was purified by column chromatography (silica gel, pet. ether/ethyl acetate) to give a yellow solid (8.6 g, 76%). An analytically pure product was obtained by trituration with diethyl ether to afford a white powder (5.8 g, 51%); m.p. 73.5°–74.5° C. $^1$H NMR (CDCl$_3$, 400 MHz): δ1.60 (s, 3H), 4.38 (s, 2H), 5.58 (s, 1H), 7.34 (m, 5H), 7.52 (t, J=7.2 Hz, 2H), 7.66 (t, J=7.2 Hz, 1H), 7.88 (d, J=4 Hz, 2H); IR (KBr): 3120, 2995, 2920, 1700, 1620, 1450, 1320, 1310, 1160, 1085, 970, 735, 685 cm$^{-1}$; MS (EI): 328 (M+), 121 (100); Analysis calc'd for C$_{18}$H$_{16}$O$_4$S: C, 65.84; H, 4.91%; Found: C, 65.70; H, 6.27%.

EXAMPLE 11

5-[(4-Chlorophenyl)sulfonyl]methyl-2,2-dimethyl-3(2H)-furanone

To a solution of sodium hydride (50% in oil, 4.0 g, 83.3 mM, washed 3×hexane) and p-chlorophenyl disulfide in tetrahydrofuran at 0° C., was added 2,2,5-trimethyl-3(2H)-furanone (3.0 g, 23.8 mM). After the addition, the reaction was stirred for three hours at room temperature. Then water (10 mL) was added, followed by 1N aqueous hydrochloric acid (90 mL). After the layers were separated, the aqueous layer was extracted with ether (2×100 mL). The combined organic layers were washed with saturated aqueous sodium chloride (2×50 mL) and dried over magnesium sulfate. The resulting solution was filtered and concentrated under reduced pressure to give a brown solid. The crude product was purified by column chromatography (silica gel, petroleum ether, then ether) to yield a pale yellow solid (8.2 g, 97%) m.p. 68°–70° C.

To a solution of furanone sulfide (7.8 g, 2.9 mM) in dichloromethane (300 mL) was added m-chloroperbenzoic acid (85%, 20.0 g, 116 mM). The reaction was stirred one hour, then 5% aqueous sodium sulfite (10 mL) was added. The mixture was stirred 10 minutes, when the organic layer was separated. The organic layer was extracted with saturated aqueous sodium bicarbonate (3×100 ml), dried over magnesium sulfate, filtered and concentrated under reduced pressure to yield a white solid. The crude product was purified by column chromatography (silica gel, petroleum ether-ethyl acetate) to afford a white solid (7.1 g, 81%). Recrystallization from carbon tetrachloride gave analytically pure material: m.p. 112°–113° C., $^1$H NMR (CDCl$_3$, 400 MHz): δ1.22 (s, 6H), 4.26 (s, 2H), 5.58 (s, 1H), 7.54 (d, J=8 Hz, 2H), 7.82 (d, J=8 Hz, 2H), MS (EI): 300 (M$^+$), 67 (100); Analysis for: C$_{13}$H$_{13}$O$_4$SCl, Calc'd: C, 51.92; H, 4.36%; Found: C, 52.28; H, 4.18%.

EXAMPLE 12

The compound of Example 12 was prepared by the procedure described in Example 1 using appropriate disulfide (ILIA).

5-[(4-Fluorophenyl)sulfonyl]methyl-2,2-dimethyl-3(2H)-furanone

Prepared in 40% yield; m.p. 118°–120° C.; $^1$H NMR (CDCl$_3$, 400 MHz): δ1.24 (s, 6H), 4.26 (s, 2H), 5.60 (s, 1H), 7.25 (dt, J$_1$=10.2 Hz, J$_2$=2 Hz, 2H), 7.92 (dd, J=10 Hz, J$_2$=1 Hz, 2H); MS (EI): 284 (M$^+$), 67 (100); Analysis calc'd for C$_{13}$H$_{13}$O$_4$SF: C, 54.92; H, 4.61%; Found: C, 55.14; H, 4.59%.

EXAMPLE 13

2,2-Dimethyl-5-(methylsulfonyl)methyl-3(2H)-furanone

To a solution of sodium hydride (50% in oil, 6.6 g, 138 mM, washed 3× with hexane) and dimethyl sulfide (8 mL, 87 mM) in tetrahydrofuran (200 mL) at 0° C. was added 2,2,5-trimethyl-3(2H)-furanone (5.0 g, 39.7 mM). After the addition, the reaction was warmed to RT and stirred overnight. The reaction was then poured slowly into cold 1N aqueous hydrochloric acid (50 mL). After separation of layers, the aqueous layer was extracted with ether (2×100 mL). The combined ether extracts were washed with saturated aqueous sodium chloride (100 mL), dried over magnesium sulfate, filtered and concentrated under reduced pressure to afford an amber oil (8.7 g, 100%): $^1$H NMR (CDCl$_3$, 200 MHz): δ1.36 (s, 6H), 2.18 (s, 6H), 4.48 (s, 1H), 5.58 (s, 1H).

To a solution of disulfide (9.5 g, 44.1 mmol) and thiophenol (18 mL, 179 mM) in tetrahydrofuran (250 mL) was added sodium hydride (50%, 0.86 g, 17.9 mM). The resulting mixture was stirred for an hour and quenched with 1N aqueous hydrochloric acid (25 mL). After dilution of the reaction mixture with saturated aqueous sodium chloride (250 mL), the aqueous layer was extracted with ether (2×100 mL). The combined ethereal extracts were washed with saturated aqueous sodium chloride (50 mL) and dried over magnesium sulfate. The ether solution was filtered and concentrated under reduced pressure to afford a yellow liquid. The crude product was purified by column chromatography (silica gel, hexane then ether) to afford a light yellow liquid (7.2 g, 88% from ketone): $^1$H NMR (CDCl$_3$, 200 MHz): 1.25 (s, 6H), 2.81 (s, 3H), 3.95 (s, 2H), 5.58 (s, 1H).

To a solution of methylthiofuranone (6.7 g, 38.9 mM) in dichloromethane (500 mL) at room temperature, was added 85% m-chloroperbenzoic acid (14.8 g, 85.6 mM). After the reaction was stirred 30 minutes, 5% aqueous sodium sulfite (100 mL) was added. The reaction was stirred 10 minutes when the organic layer was separated. The organic layer was washed with saturated aqueous sodium bicarbonate (3×100 mL), dried over magnesium sulfate, filtered and concentrated under reduced pressure to give a white solid. The crude product was purified by column chromatography (silica gel, petroleum ether-ethyl acetate) to afford a white crystalline solid (5.1 g, 65%). Trituration of product with ether gave an analytically pure product: m.p 99°–100° C., $^1$H NMR (CDCl$_3$, 400 MHz): δ1.35 (s, 6H), 3.13 (s, 3H), 4.57 (s, 2H), 5.75 (s, 1H); MS(EI): 204 (M$^+$), 67 (100); IR (KBr): 3410, 2950, 2920, 1710, 1605, 1350, 1340, 1240 cm$^{-1}$; Analysis calc'd for C$_8$H$_{12}$O$_4$S: C, 47.04; H, 5.92%; Found: C, 47.01; H, 5.64%.

EXAMPLE 14

Example 14 was prepared by the procedure described in Example 13, using the appropriate disulfide (IIIA).

2,2-Dimethyl-5-[[4-(1,1-dimethylethyl)phenyl]sulfonyl]methyl-3(2H)-furanone

Prepared in 63% yield; mp 108° C.–110° C.; $^1$H NMR (CDCl$_3$, 400 MHz) δ1.18 (s, 6H), 1.32 (s, 9H), m 4,25 (s, 2H), 7.56 (d, J=4.4 Hz, 2H), 7.80 (d, J=4.4 Hz, 2H); MS (EI): 322 (M$^+$), 67 (100); Analysis calc'd for C$_{17}$H$_{22}$O$_4$S: C, 63.33; H, 6.88%; Found C, 63.33, H, 6.71%.

EXAMPLE 15

4-[(4-Fluorophenyl)sulfonyl]methyl-2,2-dimethyl-3(2H)-furanone

A solution of 2,2-dimethyl-3(2H)-furanone (3.0 g, 26.8 mM), p-fluorothiophenol (3.5 g, 21.9 mM), 37 percent aqueous formaldehyde (8.4 g, 10.4 mM) and triethylamine (2.7 g, 26.8 mM) in ethanol (75 mL) was heated at reflux for 3 days. After the reaction cooled to room temperature, the mixture was diluted with water (100 mL) and extracted with diethyl ether (3×100 mL). The combined ethereal extracts were washed with H$_2$O (2×50 mL), dried over magnesium sulfate, filtered and concentrated under reduced pressure to yield a yellow liquid (7.2 g, >100%): $^1$H NMR (CDCl$_3$, 200 MHz): δ1.32 (s, 6H), 3.52 (s, 2H), 6.95 (m, 2H), 7.31 (m, 2H), 7.85 (s, 1H).

To a solution of furanone sulfide (2.4 g, 9.5 mM) in dichloromethane (150 mL), was added m-chloroperbenzoic acid (85%, 4.9 g, 28.5 mM). The resulting solution was stirred for four hours. The solution was washed with 0.5M aqueous sodium sulfite (50 mL) and saturated aqueous sodium bicarbonate (2×20 mL). The resulting organic layer was dried over magnesium sulfate, filtered and concentrated under reduced pressure to yield a white solid that was triturated with ethyl ether to yield white crystals (1.1 g, 41%), mp 159°–160° C. $^1$H NMR (CDCl$_3$, 400 MHz): δ1.31 (s, 6H), 3.95 (s 2H), 7.25 (m, 2H), 7.85 (m, 2H), 8.39 (s, 1H); MS (EI) 284 (M$^+$), 125

(100); Analysis calc'd for $C_{13}H_{13}O_4SF$: C, 54.92; H, 54.61%; Found: C, 54.64; H, 4.64%

EXAMPLES 16 and 17

The compounds of Examples 16 and 17 were prepared by the procedure described in Example 15 from 2,2-dimethyl-3(2H)-furanone (VIIA) and the appropriate mercaptan (VIIIA).

EXAMPLE 16

2,2-Dimethyl-4-[[4-(1,1-dimethylethyl)phenyl]sulfonyl]methyl-3(2H)-furanone

Prepared in 13% yield; m.p. 88°-90° C.; $^1$H NMR (CDCl$_3$, 400 MHz): $\delta$1.39 (s, 6H), 1.40 (s, 9H), 3.83 (s, 2H), 8.44 (s, 1H); MS (EI): 246 (M+), 127 (100); Analysis calc'd for $C_{11}H_{14}O_4S$: C, 53.64; H, 7.36%; Found: C, 43.51; H, 4.59%.

EXAMPLE 17

4-[(1,1-Dimethylethyl)sulfonyl]methyl-2,2-dimethyl-3(2H)-furanone

Prepared in 23% yield; m.p. 120°-122° C.; $^1$H NMR (CDCl$_3$, 400 MHz): $\delta$1.20 (s, 6H), 1.31 (s, 9H), 3.95 (s, 2H), 7.37 (d, J=4.8 Hz, 2H), 7.62 (d, J=4.8 Hz, 2H), 8.36 (s, 1H); MS (EI): 322 (M+); 125 (100); Analysis calc'd for $C_{17}H_{22}O_4S$: C, 63.33; H, 6.88%; Found: C, 63.00; H, 7.04%.

EXAMPLE 18

4-[(1,1-Dimethylethyl)sulfonyl]methyl-2-(4-fluorophenyl)-2-methyl-3(2H)-furanone To a solution of 2,3-butadione (5.1 mL, 58 mM) in diethyl ether (250 mL) at −78° C., was added dropwise a 2.0M solution of p-fluorophenylmagnesium bromide in ethyl ether (3.2 mL, 64 mM). After the addition, the reaction was allowed to warm to room temperature. Then 1N aqueous hydrochloric acid (75 mL) was added and the layers separated. The organic layer was washed with saturated aqueous sodium chloride (50 mL), dried over magnesium sulfate, filtered and concentrated under reduced pressure to give a brown oil (10.2 g, 96%); $^1$H NMR (CDCl$_3$, 200 MHz): $\delta$1.73 (s, 3H), 2.05 (s, 3H), 4.5 (br s, 1H), 7.03 (m, 2H), 7.41 (m, 2H).

To a solution of sodium hydride (97%, 2.2 g, 88.6 mM) in tetrahydrofuran (250 mL) at 45° C., was added a solution of ketoalcohol (9.5 g, 52.1 mM) and ethyl formate (3.9 g, 52.1 mM) in tetrahydrofuran (50 mL). The reaction was then heated at 45° C. for four hours. The cooled reaction was quenched with a solution of acetic acid (5.4 g, 90 mM) in water (100 mL) and ethyl ether (250 mL). The layer were separated. The organic layer was washed with saturated aqueous sodium bicarbonate (2×50 mL) and saturated aqueous sodium chloride (50 mL). The resulting solution was dried over magnesium sulfate, filtered and concentrated under reduced pressure to give an amber oil (10.4 g, 95%) which was used without further purification. $^1$H NMR (CDCl$_3$, 200 MHz): $\delta$1.70 (s, 3H), 2.65 (m, 2H), 4.75 (br s, 1H), 5.95 (d, J=1 Hz, 1H).

To a solution of hemiketal (10.4 g, 49.5 mM) in dichloromethane (350 mL) at room temperature was added trifluoroacetic anhydride (8.8 mL, 62.5 mM). After the reaction stirred for one hour, triethylamine (18.2 mL, 130.3 mL) was added to the reaction. The reaction was further stirred 15 minutes. Then the solution was washed with water (2×100 mL), dried over magnesium sulfate, filtered and concentrated under reduced pressure to give an amber oil. Purification by column chromatography (silica gel, petroleum ether-ethyl acetate) afforded a red liquid (5.9 g, 59%). $^1$H NMR (CDCl$_3$, 200 MHz): $\delta$1.70 (s, 3H), 5.67 (d, J=2 Hz, 1H), 7.04 (t, J=8 Hz, 2H), 7.45 (dd, J$_1$=8 Hz, J$_2^2$=4 Hz, 2H), 8.33 (d, J=2 Hz, 1H).

A solution of enone (1.0 g, 5.2 mM) in dioxane (6 mL) was saturated with hydrochloric acid gas. The reaction was then heated to 90° C. for six hours while hydrochloric acid gas was introduced into the reaction. After the reaction was cooled, saturated aqueous sodium chloride was added (100 mL). The aqueous layer was extracted with ethyl ether (3×50 mL). The combined ethereal extracts were washed with saturated aqueous sodium chloride (25 mL), dried over magnesium sulfate, filtered and concentrated under reduced pressure to afford a brown liquid (1.25 g, 100% ). The residue was used without purification. $^1$H NMR (CDCl$_3$, 200 MHz): $\delta$1.74 (s, 3H), 4.23 (s, 2H), 7.05 (t, J=8 MHz, 2H), (dd, J$_1$=8 Hz, J$_2$=4 Hz, 2H), 8.41 (s, 1H).

To a suspension of sodium hydride (97%, 235 mg, 9.5 mM) in dimethylformamide (25 mL) was added dropwise t-butylthiol (1.1 mL, 9.5 mM). After the solution was stirred 30 mins, a solution of chloromethylene enone (1.9 g, 7.9 mM) in dimethylformamide (25 mL) was added dropwise. The reaction was stirred two hours and water (30 mL) was added to the reaction. The mixture was extracted with ethyl ether (3×100 mL). The combined ethereal extracts were washed with water (50 mL), dried over magnesium sulfate, filtered and concentrated under reduced pressure to give a brown oil (2.1 g) that was used without purification. $^1$H NMR (CDCl$_3$, 200 MHz): $\delta$1.31 (s, 9H), 1.70 (s, 3H), 3.30 (s, 2H), 7.04 (t, J=7 Hz, 2H), 7.47 (dd, J$_1$=8 Hz, J$_2$=4 Hz, 2H).

To a solution of sulfide enone (2.1 g, 7.1 mM) in dichloromethane (200 mL) was added m-chloroperbenzoic acid (85%, 3.09 g, 17.8 mM). The resulting solution was stirred four hours. The solution was washed with 0.5M aqueous sodium sulfite (50 mL) and saturated aqueous sodium bicarbonate (2×20 mL). The resulting organic layer was dried over magnesium sulfate, filtered and concentrated under reduced pressure to yield a white solid. The product was purified by column chromatography (silica gel, hexane-ethyl acetate) to afford a white solid (1.5 g, 58% from chloromethylene enone); mp 105°-107° C. $^1$H NMR (CDCl$_3$, 400 MHz): d 1.38 (s, 9H), 1.75 (s, 3H), 3.85 (s, 2H), 7.05 (t, J=8.8 Hz, 2H), 7.46 (dd, J$_1$=8.8 Hz, J$_2$=4 Hz, 2H), 8.65 (s, 1H); MS (EI) 327 (M+), 205 (100); Analysis calc'd for $C_{16}H_{19}O_4SF$: C, 58.88; H, 4.36%; Found: C, 59.07; H, 5.69%.

EXAMPLES 19 and 20

The compounds of examples 19 and 20 were prepared by the procedure described in Example 18 from 2,3-butadione XI and the appropriate Grignard reagent XII.

EXAMPLE 19

4-[(1,1-Dimethylethyl)sulfonyl]methyl-2-(4-chlorophenyl)-2-methyl-3(2H)-furanone Prepared in 43% yield; mp 148°-149° C. $^1$H NMR (CDCl$_3$, 400 MHz): $\delta$1.38 (s, 9H), 1.74 (s, 3H), 3.84 (s, 2H), 7.33 (d, J=4.4 Hz, 2H), 7.43 (d, J=4.4 Hz, 2H), 8.65 (s, 1H); MS (EI): 343 (M+), 287 (100); Analysis calc'd for $C_{16}H_{19}O_4ClS$: C, 56.05; H, 5.59%; Found: C, 55.95; H, 5.89%.

EXAMPLE 20

4-[(1,1-Dimethylethyl)sulfonyl]methyl-2-methyl-2-phenyl-3(2H)-furanone

Prepared in 27% yield, 126°–127° C. $^1$H NMR (CDCl$_3$, 400 MHz): δ1.37 (s, 9H), 1.78 (s, 3H), 3.83 (d, J=16 Hz, 1H), 3.87 (d, J=16 Hz, 1H), 7.36 (m, 3H), 747 (d, J=12 Hz, 2H), 8.67 (s, 1H); MS (EI): 309 (M+), 253 (100); Analysis calc'd for $C_{16}H_{20}O_4S$: C, 62.31; H, 6.54%; Found: C, 62.20; H, 6.59%.

The blood-glucose lowering activity and inhibition of cholesterol absorption activity of the compounds of the present invention are demonstrated by the following pharmacological tests:

The db/db (C57BL/KsJ) mouse exhibits many metabolic abnormalities that are associated with non-insulin dependent diabetes melitus (Type II) in humans. The animals are obese, glucose intolerant and have fasting hyperglycemia which is sometimes accompanied by a paradoxical hyperinsulinemia. The blood glucose lowering activity of the compounds of formulas I and II of this invention were demonstrated in experiments using such diabetic (db/db) mice, according to the procedure described below.

On the morning of Day 1, 12–15 mice [male db/db (C57BLKsJ), Jackson Laboratories, 2 to 7 months of age and body weight 35 to 60 g] were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, the mice were randomly assigned into 3–5 groups (4–5 mice per group) of equivalent mean plasma glucose levels:

Group A: Vehicle control
Group B: Positive control (ciglitazone)
Group C: 1st Test drug
Group D: 2nd Test drug
Group E: 3rd Test drug On the afternoon of Days 1, 2 and 3 the vehicle, control or test drugs were administered (p.o.) to the ad libitum fed mice. The positive control, ciglitazone [(±)-5-[4-[(1-methylcyclohexyl]benzyl]-thiazolidine-2,4-dione] see Fujita et al. Diabetes, 32, 804 (1983), was given by gavage at a dose of 100 mg/kg/day. The test compounds were given by garage at a dose of 100 mg/kg/day. The fourth and final dose was administered on the morning of day 4, after the mice had been fasted for 18 h. A blood sample was collected immediately preceeding the last dose, followed by samples collected at 90 and 120 min after drug administration. Insulin is immediately administered to each mouse after the 120 min sample. Serial blood samples were collected at 45 and 120 min after administration. The plasma was separated and the levels of glucose in plasma determined by the Abbot VP analyzer.

Analysis of variance followed by Dunnett's multiple comparison (one-sided) was used to estimate the degree of statistical significance of the difference between the vehicle control group and the individual drug-treated groups. A drug was considered active, at the specific dose administered, if the difference of the plasma glucose level has ap<0.10.

The actual difference between the mean percent change of blood glucose levels of the vehicle and the drug treated group is reported in Table 1.

TABLE 1

| Compound | Blood Glucose Levels % Change from Vehicle 100 (mg/kg) |
|---|---|
| Ex. 1 | −30 |
| Ex. 2 | −21 |
| Ex. 3 | −21 |
| Ex. 4 | −30 |
| Ex. 5 | −23 |
| Ex. 6 | −25 |
| Ex. 7 | −38 |
| Ex. 8 | −42 |
| Ex. 9 | −25 |
| Ex. 10 | −19 |
| Ciglitazone (Positive Control) | −24 to −50 |

Examination of the results tabulated in Table 1 shows that the compounds of this invention are well suited as antidiabetic agents for they lower blood glucose levels in diabetic (db/db) mice.

Cholesterol absorption was measured in normal rats following simultaneous oral doses of the test compounds and radioactive cholesterol according to the method of Cayen and Dvornik except that [$^{14}$C] cholesterol in propylene glycol and olive oil (vehicle for test compound) were used. Serum radioactivity was measured at 6 hr [Cayen, M. N. and Dvornik, D., J. Lipid Res., 20, 162 (1979)]. Example 1 showed a 79% decrease in cholesterol absorption at 100 mg/kg. Example 7 showed a 58% decrease in cholesterol absorption at 250 mg/kg. Example 10 showed a 35% decrease in cholesterol absorption at 250 mg/kg.

The cytoprotective and antiulcer activity of the compounds of the present invention is demonstrated by the following pharmacological test.

ETHANOL INDUCED CYTOTOXICITY IN RATS

The purpose of this assay is to evaluate the effectiveness of the compounds of the present invention in preventing the formation of gastric mucosal lesions produced by ethanol. The assay is based on A. Robert, et at: Gastroenterology, 77: 433–443, 1979.

Male Sprague-Dawley rats weighing between 120–150 grams were fasted for 24 hours prior to the experiment (water ad libitum). At least two hours before dosing, the animals were placed in individual cages with wire grid bottoms and denied access to water.

Drug Preparation and Administration

Ethanol was administered orally at 1 mL per animal. The compounds of the present invention were dissolved in water or suspended in water with 0.5% carboxymethylcellulose and administered orally at a dose based on an appropriate standard giving $ED_{50}$ to $ED_{75}$ response of cytoprotective activity.

Methodological Details

The rats were randomly divided into groups of equal number, ordinarily 10 to a group. The rats were weighed and the individual weights were recorded. Exactly 1 hour prior to the administration of ethanol, the screening group was treated with the compounds of the present invention, and the control group with the vehicle. One hour after administering the ethanol the animals were sacrificed by cervical dislocation The stomachs were removed, cut along the greater curvature and cleansed of all debris with tap water. The stomachs were set aside and kept moist with saline until the lesions were scored.

Sample Analysis

Macroscopic lesions on the gastric mucosa were numerically graded. The final grade assigned a stomach was the sum of all the grades.

| Grade | Description (Approximate length of lesion) |
| --- | --- |
| 0 | no lesion |
| 1 | 2 mm or less |
| 2 | 4 mm |
| 3 | 6 mm |

Streaks longer than 6 mm are graded in multiples of 2 mm.

Interpretation of data

The degree of cytotoxicity occurring in each group is represented as the mean ±S.E.M.

Presentation of Results and Criteria for Activity:

The mean of each treatment group was compared to the control group and expressed as the % inhibition of lesion formation. The results are set forth in Table 2

TABLE 2

| | Ethanol Induced Cytotoxicity in Rats | | |
| --- | --- | --- | --- |
| | Test Results | | |
| EX | % Inhibition | Dose mg/kg | m.p. (°C.) |
| 11 | 44 | 25 | 112–113 |
| 12 | 6 | 25 | 118–120 |
| 13 | 54 | 25 | 99–100 |
| 14 | 43 | 25 | 108–110 |
| 15 | 42 | 25 | 159–160 |
| 16 | 30 | 25 | 120–122 |
| 17 | 87 | 25 | 88–90 |
| 18 | 80 | 10 | 105–107 |
| 19 | 45 | 10 | 148–149 |
| 20 | 76 | 25 | 126–127 |

We claim:

1. A method for treating ulcers which comprises administering to a patient in need of such treatment, an effective amount of a compound of formula (I)

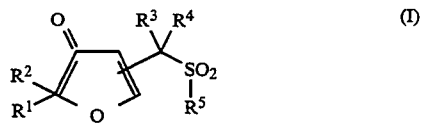

wherein $R^1$ and $R^2$ are independently alkyl containing 1 to 3 carbon atoms, phenyl or halogen substituted phenyl;

$R^3$ and $R^4$ are hydrogen;

$R^5$ is alkyl containing 1 to 6 branched or straight chain carbon atoms, substituted phenyl wherein the substituent is selected from the group consisting of alkyl containing 1 to 6 branched or straight chain carbon atoms and halogen.

* * * * *